United States Patent [19]

Heinzerling et al.

[11] Patent Number: 4,911,705
[45] Date of Patent: Mar. 27, 1990

[54] Y-JOINT FOR INFUSION EQUIPMENT

[75] Inventors: Walter C. Heinzerling, Bad Hersfeld; Wolfgang Schadt, Rotenburg, both of Fed. Rep. of Germany

[73] Assignee: Clinico Infusionstechnik GmbH & Co. med. Kunststoffprodukte KG, Bad Hersfeld, Fed. Rep. of Germany

[21] Appl. No.: 237,536

[22] Filed: Aug. 29, 1988

[30] Foreign Application Priority Data

Nov. 4, 1987 [DE] Fed. Rep. of Germany ... 8714659[U]

[51] Int. Cl.$^4$ ............................................. A61M 37/00
[52] U.S. Cl. ..................................... 604/86; 604/122; 604/201
[58] Field of Search ............... 604/284, 82, 83, 86–88, 604/122, 93, 201

[56] References Cited

U.S. PATENT DOCUMENTS

| | | | |
|---|---|---|---|
| 3,217,711 | 11/1965 | Pecina et al. | 604/81 |
| 3,332,418 | 7/1967 | Brody | 604/86 |
| 3,993,066 | 11/1976 | Virag | 604/86 |
| 4,040,996 | 9/1977 | Mittleman et al. | 604/86 |
| 4,048,995 | 9/1977 | Mittleman | 604/86 |
| 4,165,742 | 8/1979 | Gardner | 604/83 |
| 4,219,022 | 8/1980 | Genese | 604/86 |
| 4,289,129 | 9/1981 | Turner | 604/86 |
| 4,596,557 | 6/1986 | Pexa | 604/284 |
| 4,804,366 | 2/1989 | Zdel et al. | 604/88 |

FOREIGN PATENT DOCUMENTS

| | | | |
|---|---|---|---|
| 8603417 | 6/1986 | European Pat. Off. | 604/85 |
| 1099903 | 11/1983 | Fed. Rep. of Germany . | |

Primary Examiner—Dalton L. Truluck
Assistant Examiner—Denise W. DeFranco
Attorney, Agent, or Firm—Staas & Halsey

[57] ABSTRACT

A Y-joint eliminates air space between an injection member and an injection duct by inducing flow from the intake duct towards the injection membrane. The induced flow may be generated by a deflection duct or a bypass duct. In either case, fluid infusion solution is induced to flow in a direction opposite the normal flow of the discharge duct.

3 Claims, 2 Drawing Sheets

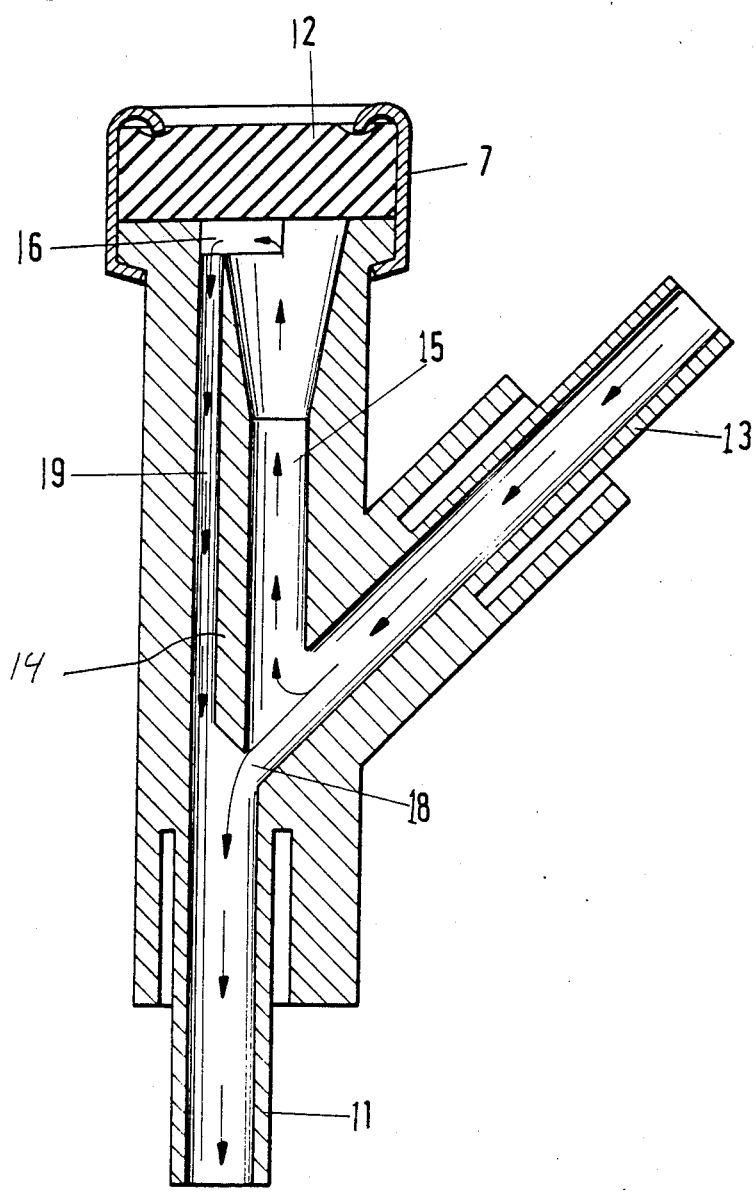

Y-JOINT FOR INFUSION EQUIPMENT

BACKGROUND OF THE INVENTION

1. Field of the Invention

The present invention relates generally to infusion equipment and, more specifically, to a Y-joint for infusion equipment.

2. Description of the Related Art

Y-joints are generally known and widely used with infusion equipment. Basically, the injection of medications during infusion takes place by passing a needle through a membrane made of latex or other suitable material.

Standard Y-joints are so named because a fork is created between an injection duct for injecting medication, and an inlet duct for introducing infusion liquid. An outlet duct is disposed beneath the point of confluence.

In a standard Y-joint, the point of confluence between the injection duct and the intake duct is defined by the point of intersection between their respective axes. This point of confluence is therefore usually below an injection membrane covering an injection port of the injection duct, such that as fluid flows through the intake duct towards the discharge duct, an air space exists in the injection duct below the injection membrane.

During initial filling of an infusion set having a standard Y-joint, a problem exists in that a residual air cushion remains in the vicinity of the injection membrane. Air pockets are dangerous and pose a potential health risk.

SUMMARY OF THE INVENTION

An object of the invention is to provide a Y-joint for use in infusion equipment which prevents the formation of air pockets at the injection membrane.

Another object of the invention is to provide a Y-joint for use in infusion equipment that prevents entrainment of air into infusion solutions.

In a preferred embodiment of the invention, a deflecting duct or a bypassing duct is provided to channel infusion fluid towards the injection membrane so as to effectively fill the entire Y-joint prior to injection of medication through the membrane. In one embodiment, the entire injection fluid fed into the intake duct of the Y-joint is deflected into the vicinity of the injection membrane so that the entire flow takes place through this area. Thus, there can be no empty space in which air can collect.

In another embodiment of the invention, a vacuum is formed in the injection duct upstream of the point of confluence of the intake duct with the injection duct. This ensures a partial injection fluid flow into the area of the injection membrane and in the area upstream of the point of confluence. Also, part of the injection fluid flows from the area of the injection membrane through a bypass duct into a corresponding part of the injection duct towards the outlet duct.

These and other features and advantages of the Y-joint of the invention will become more apparent with reference to the following detailed description and drawings.

BRIEF DESCRIPTION OF THE DRAWINGS

FIG. 2 is a diagrammatic, longitudinal cross-section of a second preferred embodiment of the present invention.

DETAILED DESCRIPTION OF THE PREFERRED EMBODIMENTS

Figure 1:
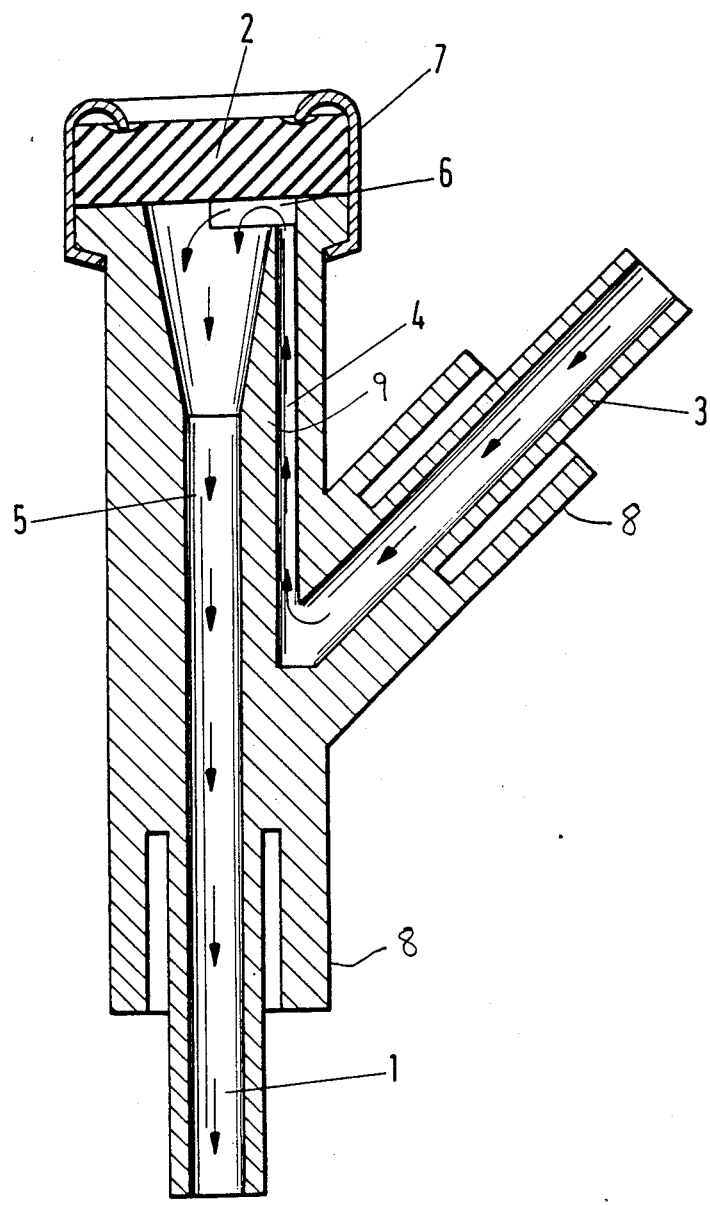
FIG. 1 is a diagrammatic, longitudinal cross-section of a first preferred embodiment of the present invention.

FIG. 1 shows a Y-joint having an intake duct 3 and an injection duct 5, and an injection member 2 which is held in place by a cap 7. Connectors 8 connect fluid conduit, such as I.V. tubing to the Y-joint.

In the embodiment of FIG. 1, the aforementioned air space is avoided by providing a deflection duct 4 which deflects fluid from the intake duct 3 upwardly in a direction opposite the normal flow through the discharge duct 1. The deflection duct 4 is in fluid communication with an uppermost portion 6 of the injection duct 5. By deflecting fluid flow into the area 6 adjacent the injection membrane 2, air spaces are avoided during the initial filling of the injection duct with infusion material. The deflecting duct 4 deflect all of the fluid flow entering the intake duct 3 towards the injection membrane 2 by using a weir 9 which is substantially parallel to the injection duct 5.

The Y-joint of FIG. 2 also includes a discharge duct 11, an injection membrane 12 with cap 17, an intake duct 13 and an injection duct 15. However, in the embodiment of FIG. 2, the injection duct is non-coaxial with the discharge duct 11 such that a portion of the fluid flow from intake duct 13 flows in an opposite direction of the discharge duct 11 towards the injection membrane 12. The point of confluence between the intake duct 13 and the discharge duct 11 defines a constriction 18 which facilitates opposite flow towards the injection membrane 12. The constriction 18 is defined by an inner wall of the Y-joint and an end of a weir 14. The weir 14 is disposed between the injection duct 15 and a bypass duct 19. The bypass duct 19 forms a connection between the area 16 adjacent to the injection membrane and a point downstream of the constriction 18.

During initial filling whereby fluid flows into the intake duct 13 for passage through discharge duct 11, a vacuum is formed such that the vacuum is communicated through the bypass duct 19 to draw fluid upwardly into the injection duct 15 to the area 16 adjacent the injection membrane. Thus, similar to the embodiment of FIG. 1, potentially harmful air spaces are avoided.

Numerous modifications and adaptations of the Y-joint of the present invention will be apparent to those so skilled in the art and thus, it is intended by the following claims to cover all such modifications and adaptations which fall within the true spirit and scope of the invention.

What is claimed is:

1. A Y-joint for use with infusion equipment comprising:
   an intake duct for introducing a fluid infusion solution,
   an injection duct in fluid communication with the intake duct and having an injection membrane connected to an open end thereof for sealing the injection duct prior to injection of medication through the injection membrane, the injection membrane being disposed upstream of the intake duct, a discharge duct in fluid communication with the intake duct and the injection duct, and flow inducing means for inducing flow of the fluid infusion solution from the intake duct to an area adjacent the injection membrane in a direction opposite that of the injected medication, wherein the flow inducing means includes a deflection duct disposed between the intake duct and the injection duct and being substantially parallel to the injection duct and extending between the injection membrane and the intake duct.

2. A Y-joint as recited in claim 1, wherein the intake duct and the injection duct converge at a point spaced from the injection membrane, and wherein the flow inducing means comprises a construction at the point of convergence between the intake duct and the injection duct, and a bypass duct disposed parallel to the injection duct and extending between an area of the injection duct adjacent the injection membrane and the injection duct downstream of the constriction.

3. A Y-joint according to claim 1, wherein the injection duct and the discharged duct are coaxial.

* * * * *